United States Patent
Back et al.

(10) Patent No.: US 7,620,526 B2
(45) Date of Patent: *Nov. 17, 2009

(54) TECHNIQUE FOR ACCESSING A DATABASE OF SERIALIZABLE OBJECTS USING FIELD VALUES CORRESPONDING TO FIELDS OF AN OBJECT MARKED WITH THE SAME INDEX VALUE

(75) Inventors: Jonathan Back, Vancouver (CA); Emmanuel A. Papoutsakis, Vancouver (CA)

(73) Assignee: Zeugma Systems Inc., Richmond (CA)

( * ) Notice: Subject to any disclaimer, the term of this patent is extended or adjusted under 35 U.S.C. 154(b) by 300 days.

This patent is subject to a terminal disclaimer.

(21) Appl. No.: 11/586,769

(22) Filed: Oct. 25, 2006

(65) Prior Publication Data
US 2008/0104009 A1    May 1, 2008

(51) Int. Cl.
G06F 17/30    (2006.01)
G06F 17/00    (2006.01)

(52) U.S. Cl. .................... 703/1; 707/3; 707/100

(58) Field of Classification Search ............... 707/1–4, 707/10, 100, 102, 103 X, 104.1, 200–205; 711/155–165, 100, 111, 205, 207; 717/103, 717/116, 165, 172; 709/203, 205, 220–225
See application file for complete search history.

(56) References Cited

U.S. PATENT DOCUMENTS 5,335,346 A * 8/1994 Fabbio ..................... 711/163
5,495,608 A * 2/1996 Antoshenkov ............. 707/3
5,680,618 A * 10/1997 Freund ..................... 707/7
5,706,455 A    1/1998 Benton et al.
5,727,197 A * 3/1998 Burgess et al. ............. 707/2
5,809,495 A    9/1998 Loaiza
5,893,097 A    4/1999 Hayata et al.

(Continued)

FOREIGN PATENT DOCUMENTS

WO    WO 95/31769    * 11/1995

(Continued)

OTHER PUBLICATIONS

Jung-Ho Ahn et al. "Index set: A practical indexing scheme for object database systems", Data & Knowledge Engineering 33 (2000) 199±217.*

(Continued)

Primary Examiner—Srirama Channavajjala
(74) Attorney, Agent, or Firm—Blakely Sokoloff Taylor & Zafman LLP

(57) ABSTRACT

A converter may be used to convert a serializable object to other file formats. A serializable objects database can be used to store these serializable objects. The serializable object database may be accessed by passing a field value, corresponding to a selected field of the serializable object, to the database. The selected field of the serializable object is marked with an index value. The database is queried using the field value to determine whether any record stored in the database includes the field value in a matching field indicated by the index value. If the query determines that the serializable objects database includes at least one record with the field value in the matching field indicated by the index value, then a plurality of field values are returned to populate a plurality of fields of the serializable object.

16 Claims, 13 Drawing Sheets

U.S. PATENT DOCUMENTS

| | | | |
|---|---|---|---|
| 5,913,029 | A | 6/1999 | Shostak |
| 5,974,418 | A * | 10/1999 | Blinn et al. .................. 707/100 |
| 5,987,506 | A | 11/1999 | Carter et al. |
| 5,991,758 | A * | 11/1999 | Ellard ............................ 707/6 |
| 6,058,423 | A | 5/2000 | Factor |
| 6,125,209 | A | 9/2000 | Dorricott |
| 6,266,660 | B1 * | 7/2001 | Liu et al. ....................... 707/3 |
| 6,457,007 | B1 | 9/2002 | Kikuchi et al. |
| 6,499,033 | B1 * | 12/2002 | Vagnozzi .................... 707/101 |
| 6,571,252 | B1 | 5/2003 | Mukherjee |
| 6,601,072 | B1 * | 7/2003 | Gerken, III ............. 707/103 R |
| 6,931,409 | B2 * | 8/2005 | Redpath ..................... 707/100 |
| 7,152,060 | B2 * | 12/2006 | Borthwick et al. ............. 707/3 |
| 7,171,419 | B2 * | 1/2007 | Redpath ..................... 707/100 |
| 7,401,338 | B1 * | 7/2008 | Bowen et al. ................ 719/328 |
| 2002/0016814 | A1 * | 2/2002 | Convent et al. ............. 709/203 |
| 2002/0049759 | A1 | 4/2002 | Christensen |
| 2002/0138353 | A1 * | 9/2002 | Schreiber et al. .............. 705/26 |
| 2003/0154202 | A1 | 8/2003 | Dinker et al. |
| 2004/0078569 | A1 | 4/2004 | Hotti |
| 2004/0139070 | A1 * | 7/2004 | Dysart et al. ................... 707/3 |
| 2004/0181537 | A1 * | 9/2004 | Chawla et al. .............. 707/100 |
| 2004/0205692 | A1 * | 10/2004 | Robinson .................... 717/100 |
| 2005/0091231 | A1 * | 4/2005 | Pal et al. ..................... 707/100 |
| 2005/0273452 | A1 * | 12/2005 | Molloy et al. .................. 707/1 |
| 2006/0112107 | A1 | 5/2006 | Jones |

FOREIGN PATENT DOCUMENTS

| | | | | |
|---|---|---|---|---|
| WO | WO 99/33002 | * | 7/1999 | |
| WO | WO 02/075600 | * | 9/2002 | |
| WO | WO 02/082260 A2 | * | 10/2002 | ...................... 9/40 |

OTHER PUBLICATIONS

"Serialization," Wikipedia, the free encyclopedia, http://en.wikipedia.org/wiki/Object_serialization (retrieved on Jul. 3, 2006).

Strumm, Michael et al., "Algorithm Implementing Shared Memory", University of Toronto, IEEE 1990, pp. 54-64.

Fleisch, Brett D., "Distributed Shared Memory in a Loosely Coupled Distributed System", University of California, Los Angeles, IEEE 1988, pp. 317-327.

Gunaseelan, L. et al., "Event Ordering in a Shared Memory Distributed System", College of Computing, Georgia Institute of Technology, IEEE 1993, pp. 256-263.

* cited by examiner

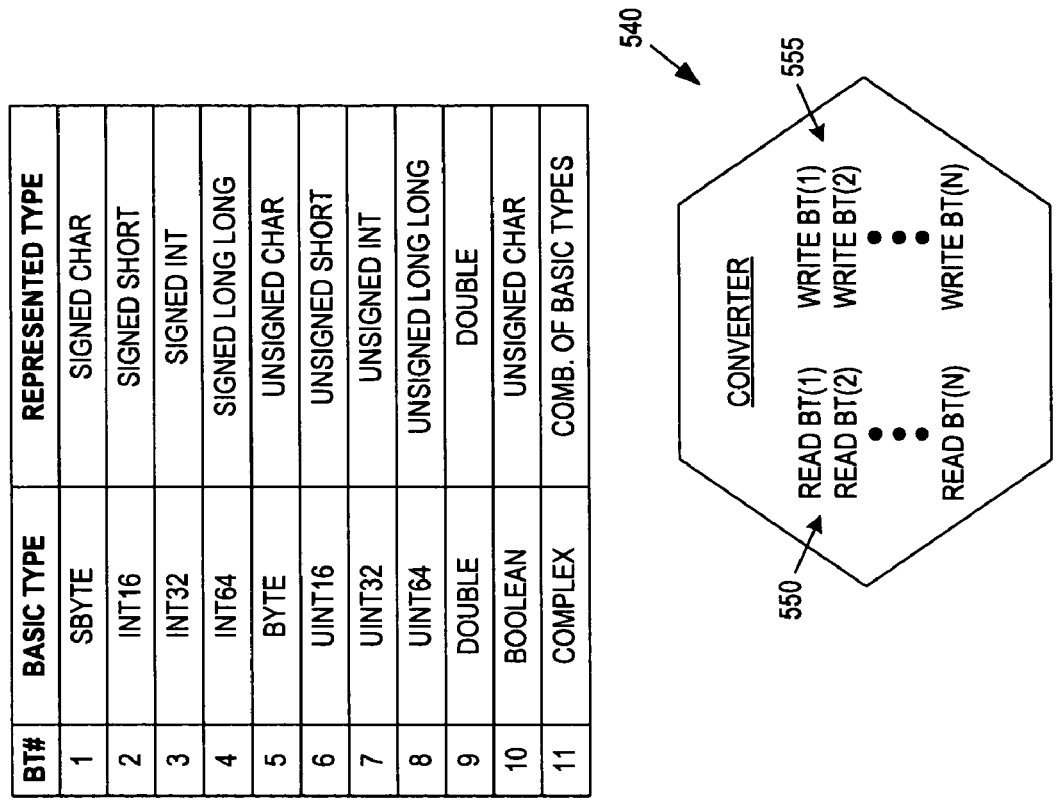
FIG. 5B
FIG. 5C
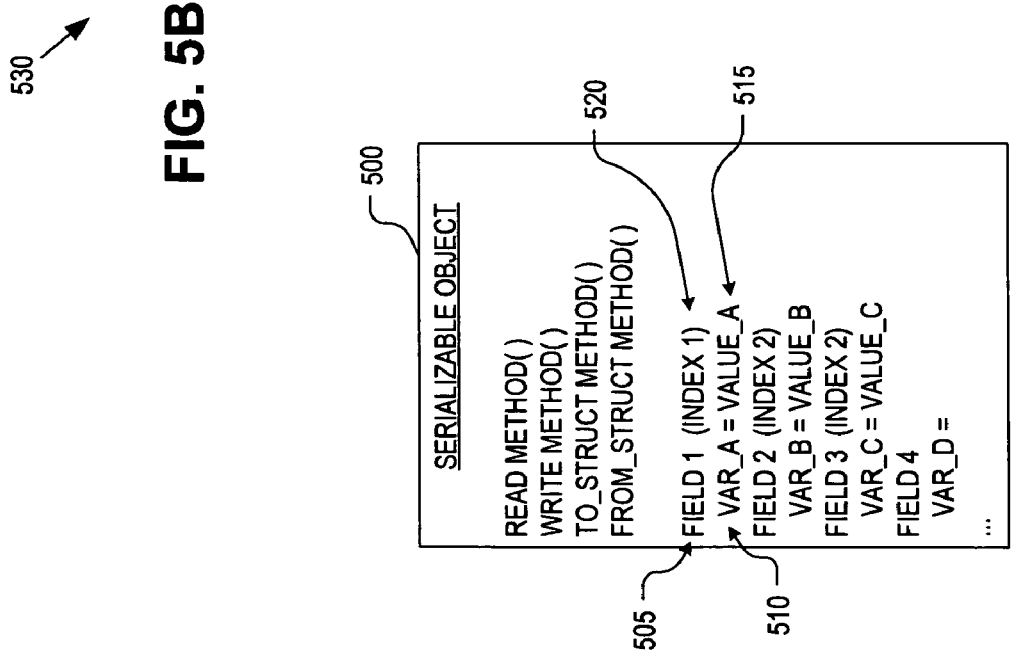
FIG. 5A

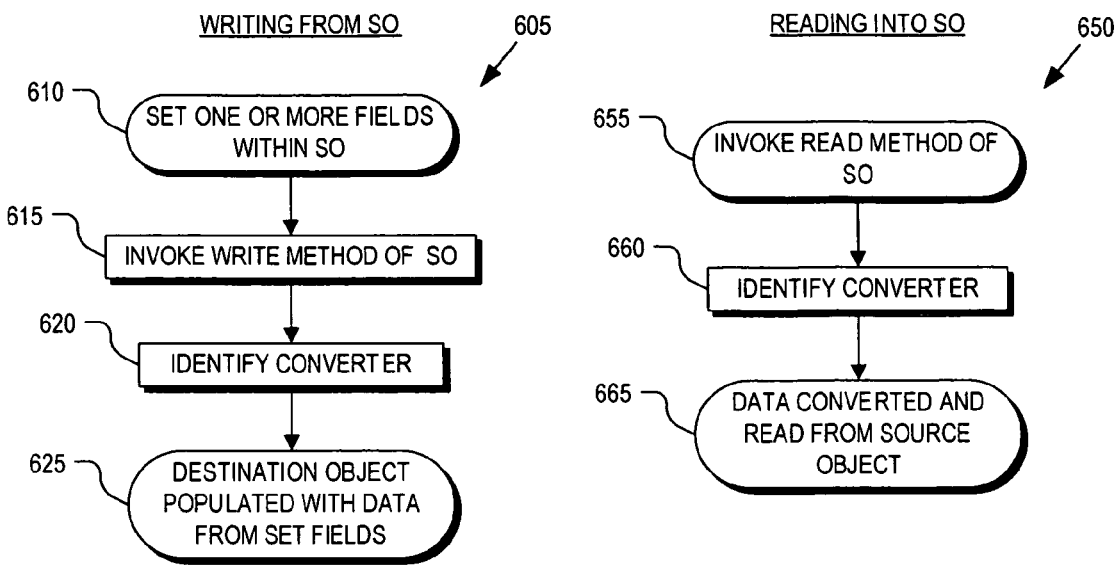
FIG. 6A
FIG. 6C
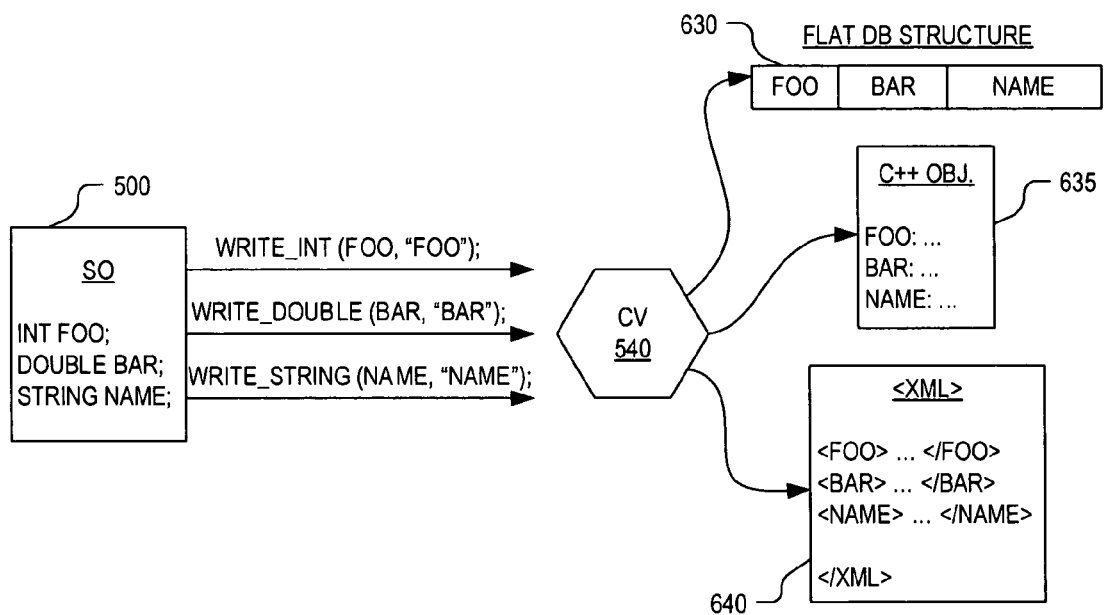
FIG. 6B

TECHNIQUE FOR ACCESSING A DATABASE OF SERIALIZABLE OBJECTS USING FIELD VALUES CORRESPONDING TO FIELDS OF AN OBJECT MARKED WITH THE SAME INDEX VALUE

TECHNICAL FIELD

This disclosure relates generally to software, and in particular but not exclusively, relates to databases.

BACKGROUND INFORMATION

FIG. 1 illustrates a conventional database system 100 including a database 105 and a database client 110. As illustrated, database 105 stores separate internal keys indexed to each record or data buffer. It is noteworthy that the internal keys are not apart of the record or the data buffer of the record, and do not contain useful data, other than for the purposes of organization and retrieval. To retrieve a particular record, database client 110 provides a key 115 to database 105, which in turn searches on it internal keys. If a match is found, then database 105 will return a record 120 indexed to the internal key that matched key 115 provided. To write data buffers or records into database 105, database client 110 may reference a database ("DB") schema 125, which includes a description of the internal structure or directory system of database 105. In short, schema 125 provides database client 110 with the knowledge necessary to access and utilize database 105.

Since database 105 merely indexes data buffers or records to internal keys, the knowledge and complexity required to run higher level queries on database 105 is pushed onto application developers of database client 110. Furthermore, since the internal keys themselves are not part of the useful data stored by database client 110, but rather independently generated values used simply for retrieving records or data buffers, the internal keys consume additional memory resources within database 105.

In an alternative conventional database system, database 105 itself may contain knowledge of the internal representation of the data buffers or records it stores to perform it own complex queries and indexing. This alternative embodiment pushes the complexities of indexing and queries onto the database developer; however, does so at the expense of performance by adding a layer of abstraction between the records stored and the database clients accessing the records.

BRIEF DESCRIPTION OF THE DRAWINGS

Non-limiting and non-exhaustive embodiments of the invention are described with reference to the following figures, wherein like reference numerals refer to like parts throughout the various views unless otherwise specified.

FIG. 5A illustrates a serializable object, in accordance with an embodiment of the invention.

FIG. 5B is a table illustrating the basic types of a serializable object, in accordance with an embodiment of the invention.

FIG. 5C illustrates a converter including read and write methods for each basic type of a serializable object, in accordance with an embodiment of the invention.

FIG. 6A is a flow chart illustrating a process for writing from a serializable object, in accordance with an embodiment of the invention.

FIG. 6B is a block diagram illustrating how a serializable object may be converted to other file formats through a converter, in accordance with an embodiment of the invention.

FIG. 6C is a flow chart illustrating a process for reading into a serializable object, in accordance with an embodiment of the invention.

DETAILED DESCRIPTION

Embodiments of a system and method for serializable objects and a serializable objects database are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Figure 1:
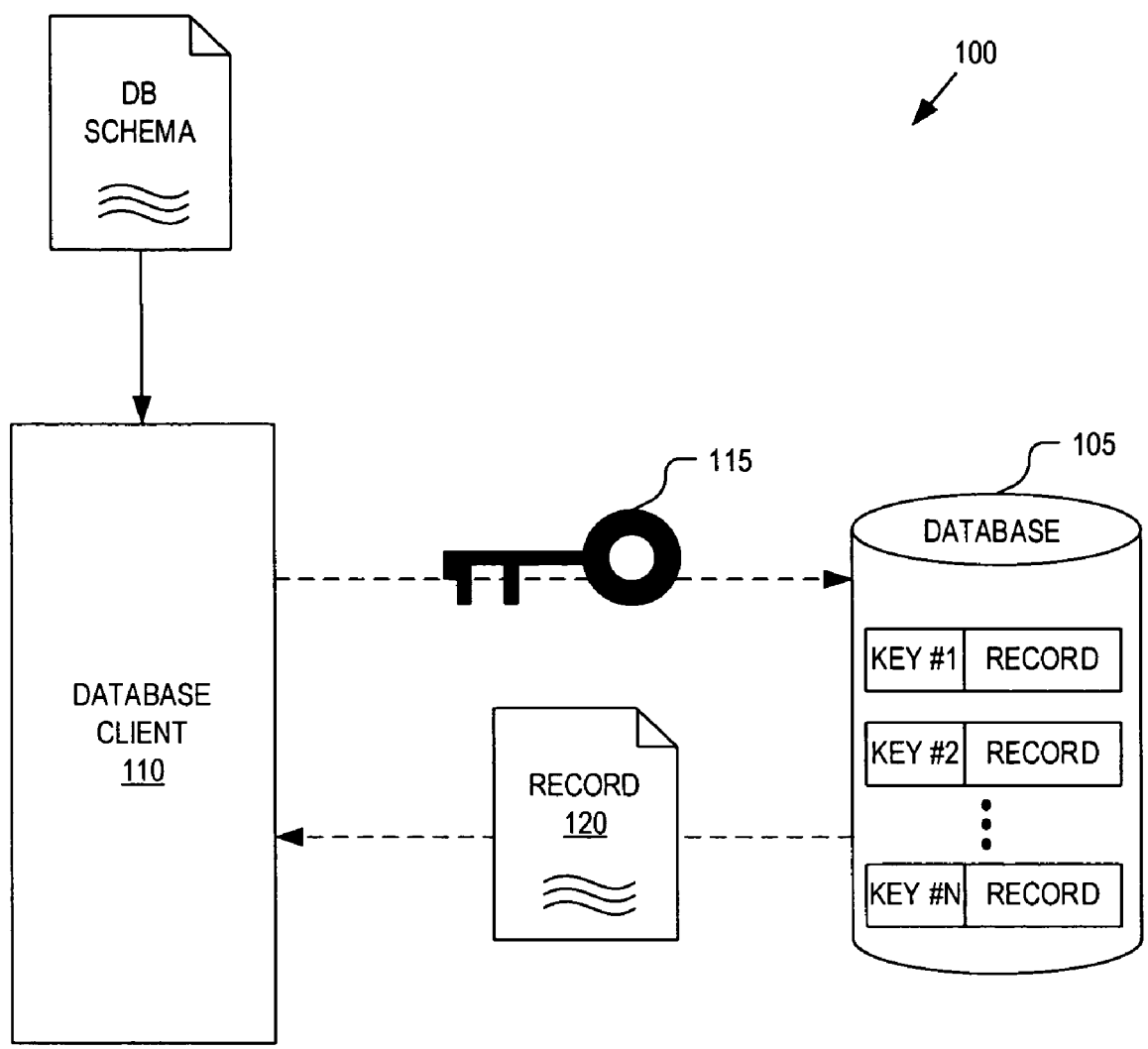
FIG. 1 (PRIOR ART) illustrates a conventional database system.
Figure 2:
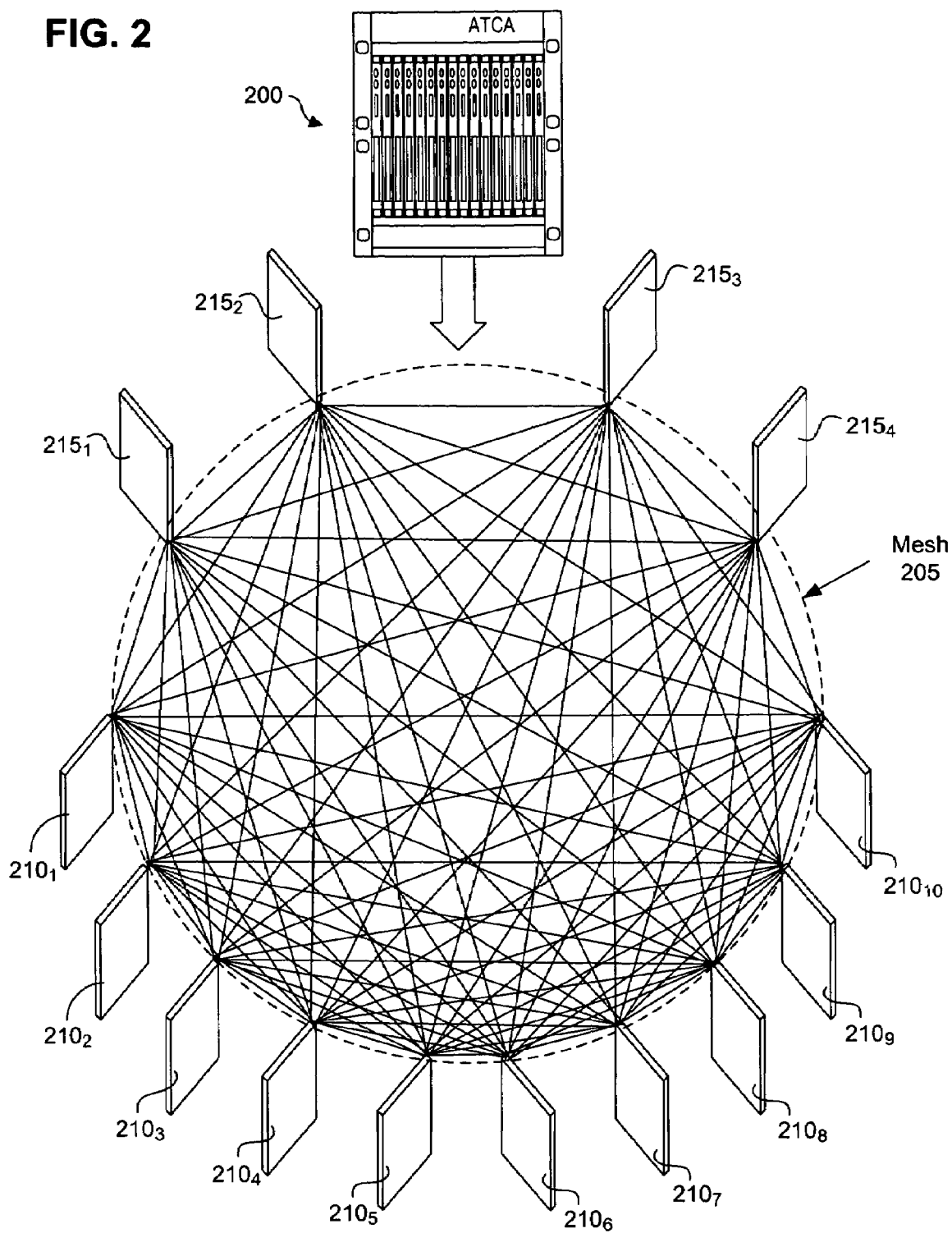
FIG. 2 is a diagram illustrating a mesh interconnect between traffic and compute modules of a network service element, in accordance with an embodiment of the invention.

FIG. 2 is a schematic diagram illustrating a mesh interconnect between traffic and compute modules of a network service element 200, in accordance with an embodiment of the invention. The illustrated embodiment of network services element 200 includes a mesh interconnect 205 coupling traffic modules 210 and compute modules 215. Each of the traffic and compute modules 210 and 215 provide the processing power to implement packet processing, routing, and other functionality. In one embodiment, network service element 200 is a service node intended to be connected between two or more networks (e.g., between core networks providing services and aggregation networks providing access to clients consuming the services), which may implement additional functionality such as traffic shaping, guarantee quality of service ("QoS"), admission protocols, or otherwise.

In the illustrated embodiment, network service element 200 is implemented using an Advanced Telecommunication and Computing Architecture ("ATCA") chassis. Mesh interconnect 205 may provide cross-connectivity between traffic and compute modules 210 and 215 with the ATCA backplane. In the exemplary configuration shown in FIG. 2, the ATCA chassis is fully populated with 14 ATCA blades (i.e., traffic and compute modules 210 and 215), with each blade installed in a respective chassis slot—in an actual implementation, the chassis may be populated with less blades or may include other types of blades in addition to compute and traffic blades. The illustrated configuration includes four compute modules $215_{1-4}$, and 10 traffic modules $210_{1-10}$, with one of the compute modules being provisioned to provide operations, administration, maintenance and provisioning functionality ("OAMP") functions. As depicted by interconnection mesh 205, each module is communicatively-coupled with every other module under the control of fabric switching operations performed by each module's fabric switch. In one embodiment, mesh interconnect 205 provides a 10 Gbps connection between each pair of modules, with an aggregate bandwidth of 280 Gbps.

In the illustrated embodiments, network service element 200 is implemented using a distributed architecture, wherein various processor and memory resources are distributed across multiple modules. To scale a system, one simply adds another module (e.g., blade). The system is further enabled to dynamically allocate processor tasks, and to automatically perform fail-over operations in response to a module failure or the like. Furthermore, under an ATCA implementation, modules may be hot-swapped without taking the system down, thus supporting dynamic scaling.

Figure 3A:
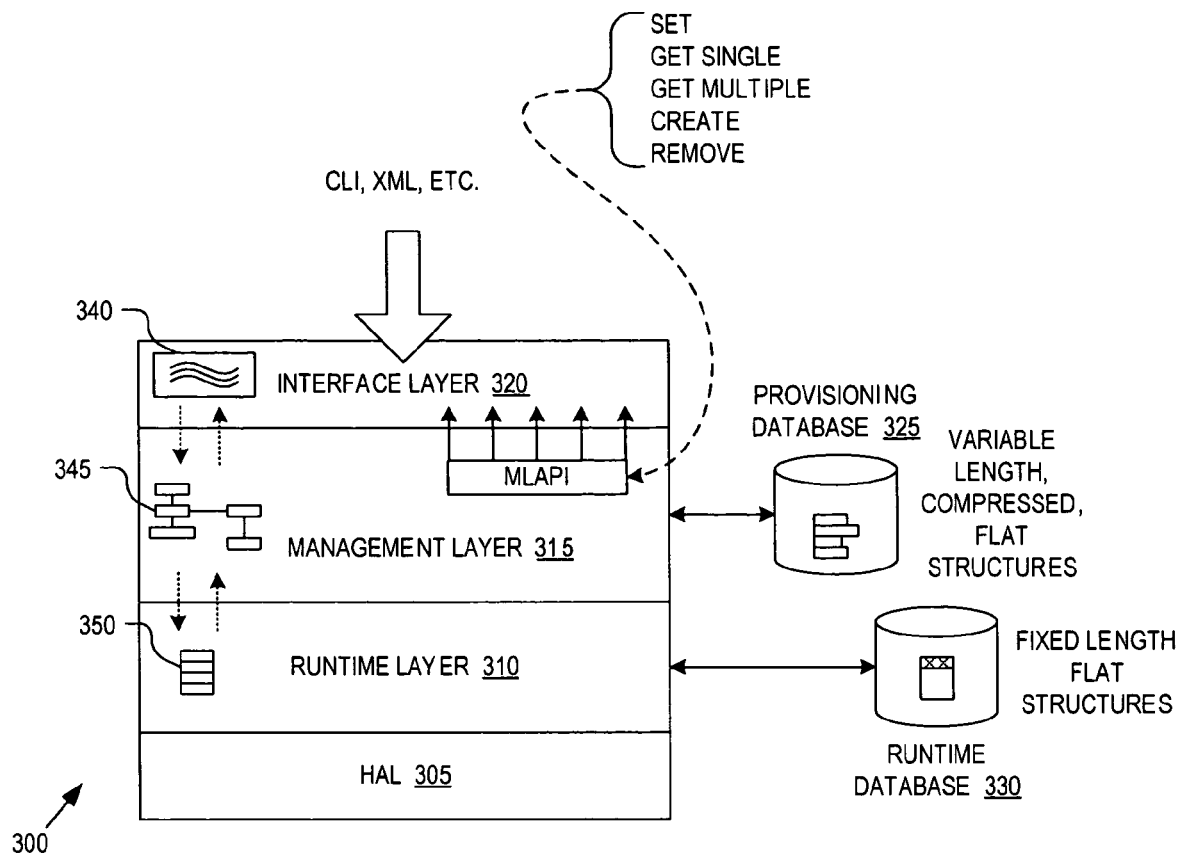
FIG. 3A is a block diagram illustrating a layered software stack executing on a module of a network service element, in accordance with an embodiment of the invention.

FIG. 3A is a block diagram illustrating a layered software stack 300 executing on a module of network service element 200, in accordance with an embodiment of the invention. The illustrated embodiment of layered software stack 300 includes a hardware abstraction layer ("HAL") 305, a runtime layer 310, a management layer 315, and an interface layer 320.

HAL 305 abstracts the underlying hardware resources to the software layers above and may include various device drivers, a kernel, software buffers, or the like. Runtime layer 310 is used to maintain dynamic state information for the modules of network service node 200, which may be in a state of flux during operation. For example, routing demons may execute in runtime layer 310 to setup and tear down route changes, to receive and process open shortest path first ("OSPF") protocol packets, or service other dynamic change requests coming up from HAL 305.

Management layer 315 services application programming interface ("API") calls from interface layer 320 and translates the calls into data, typically to be stored into a provisioning database 325 or occasionally into a runtime database 330. The APIs are published into interface layer 320 via a management layer API ("MLAPI"), which may provide a variety of APIs for accessing the databases. For example, the MLAPI may publish five APIs into interface layer 320 including a set API, a get API, a get multiple API, a create API, and a remove API. Management layer 315 typically facilities the provisioning of static attributes assigned to the modules of network service node 200. For example, static attributes may include port assignments, the existence (or lack thereof) of a module in a slot, power settings, a registry of applications executing on each module, and the like.

Finally, interface layer 320 proves an access layer to enable a user (e.g., network administrator or other Information Technology ("IT") technician) to interface with network service element 200 and the lower layers of layered software stack 300. For example, the user may invoke any of the APIs published by the MLAPI using a command line interface ("CLI") to get (e.g., retrieve) one or more records stored in provisioning database 325 or runtime database 330, create a new record, remove (e.g., delete) an existing record therefrom, or set an attribute of an object existing in lower layers of layered software stack 300. In other cases, the interface layer 320 may enable the user to push user/data files (e.g., extensible markup language ("XML") files, etc.) down to the lower layers through one or more converters.

As mentioned, interface layer 320 enables a user to push in data files 340 from external sources. Data files 340 may be XML files, C objects, C++ objects, C# objects, Java objects, or otherwise. As a data file 340 is pushed down to management layer 315, layered software stack 300 may convert data file 340 into a serializable object 345. A serializable object ("SO") is a software object that lends itself well to serialization and which is typically a complex of linked memory structures. As SO 345 is pushed further down to runtime layer 310, SO 345 may be converted into a flat structure 350. Flat structure 350 typically is a fixed length contiguous memory structure which may be quickly and easy manipulated in memory and therefore well suited for the high speed, dynamic environment of runtime layer 310.

Provisioning database 325 may be used to store provisioning data for setting static or semi-static attributes of network service element 200, while runtime database 330 may be used to store runtime data arriving on datapaths rising up from HAL 305. In one embodiment, provisioning database 325 may convert SO 345 into variable length, compressed, flat memory structures, prior to storing SO 345, while runtime database 330 may simply store flat structure 350 as a fixed length, uncompressed, flat structure. Since runtime layer 310 manages high speed, dynamically changing events, it is reasonable to tradeoff memory consumption (e.g., fixed length, uncompress structures) in exchange for low latency, high speed access to runtime database 330. In contrast, management layer 315 typically manages static or semi-static attributes, therefore compressed, variable length structures are advantages, even at the expense of incurring some processing overhead related to accessing variable length structures.

Figure 3B:
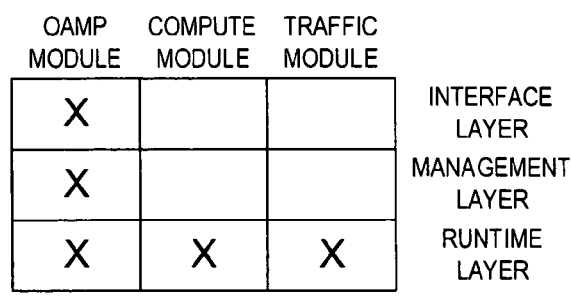
FIG. 3B is a table illustrating which layers of a layered software stack execute on an OAMP module, a compute module, or a traffic module of a network service element, in accordance with an embodiment of the invention.

FIG. 3B is a table illustrating how software components of layered software stack 300 may be distributed across multiple modules of network service element 200, in accordance with an embodiment of the invention. As illustrated, an OAMP module (which may be one of compute modules 215 selected to implement OAMP functionality) includes runtime layer 310, management layer 315, and interface layer 320. In contrast, ordinary compute modules 215 and traffic modules 210 may only execute runtime layer 310.

Figure 4A:
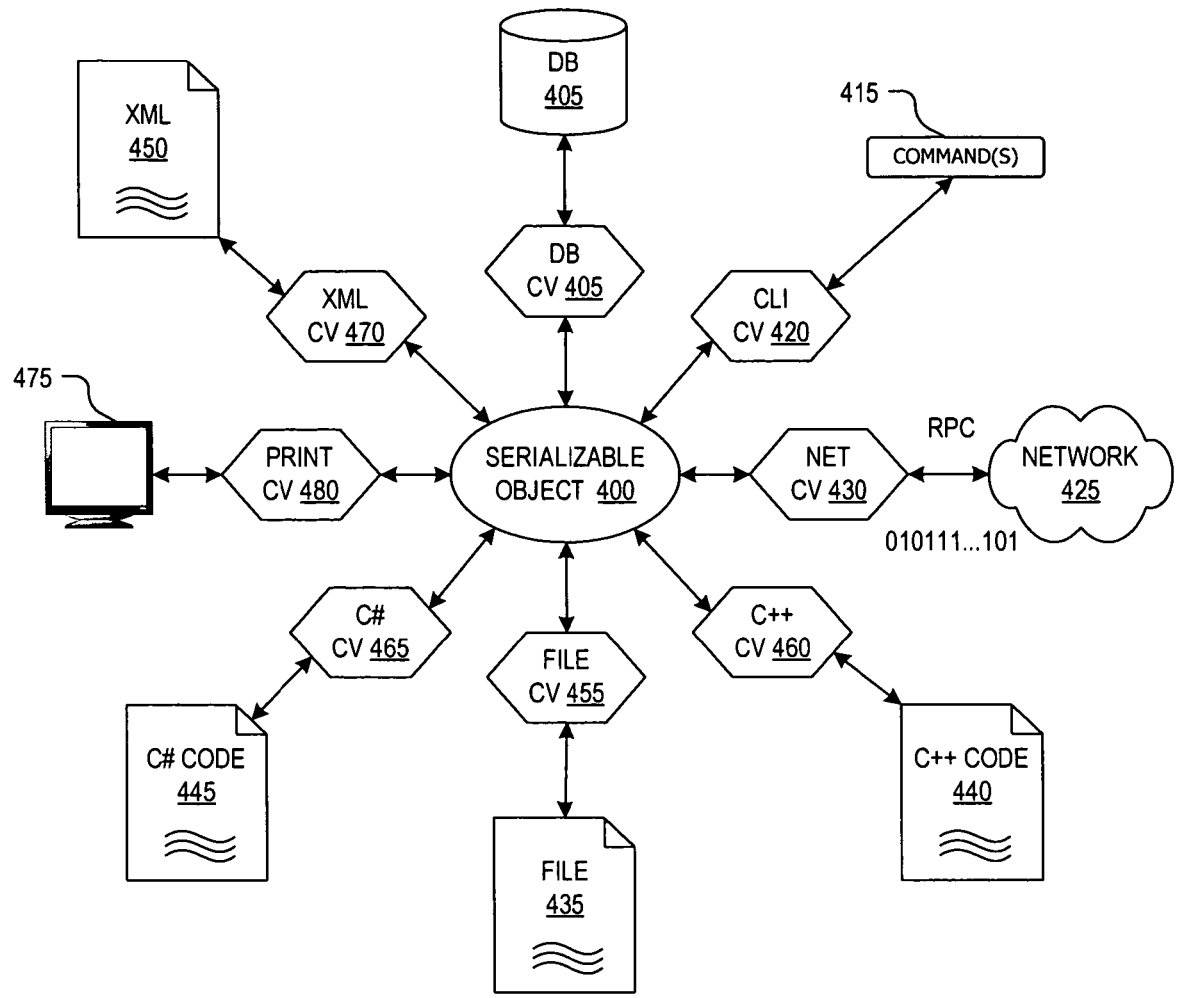
FIG. 4A is a block diagram illustrating how converters can convert a serializable object into a variety of different data formats, in accordance with an embodiment of the invention.

FIG. 4A is a block diagram illustrating how converters can convert serializable objects into a variety of different data formats, in accordance with an embodiment of the invention. As illustrated, an SO 400 may be written to or retrieved from a database 405 via a database ("DB") converter ("CV") 410, may read in commands from a CLI 415 via a CLI CV 420, may write to or read from a network connection 425 via a network ("NET") CV 430, may write to or read from a variety of file formats (e.g., generic file 435, C++ code 440, C# code 445, XML file 450, etc.) via a variety of corresponding converts (e.g., generic file CV 455, C++ CV 460, C# CV 465, XML CV 470, etc.), output text to a display 475 via a print CV 480, or the like.

SO 400 may operate as a sort of intermediary between the various file formats and provides a sort of common currency within a processing system between various entities, which otherwise communicate in a different language or format. SO 400 is amenable to serialization and conversion between some or all of the various file formats listed above, as well as others. Generic file CV 455 is included in FIG. 4A to illustrate that converters may be provided to convert SO 400 to a number of different file types beyond those illustrated in FIG. 4A. For example, file 435 may represent a Java file or any other file type or format. In one embodiment, the converters are software modules that are generated and linked to endpoints (e.g., DB 405, CLI 415, network 425, file 435, C++ code 440, C# code 445, XML file 450, display 475, etc.) and may be invoked by SO 400 to read from or write to the selected endpoint.

Figure 4B:
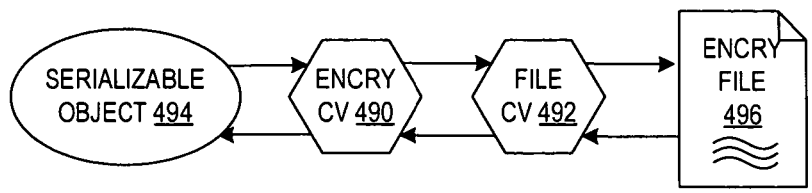
FIG. 4B is a block diagram illustrating how two converters may be linked in series, in accordance with an embodiment of the invention.

FIG. 4B is a block diagram illustrating how two or more converters may be linked in series, in accordance with an embodiment of the invention. In one embodiment, multiple CVs may be linked together or "daisy chained" to enable multiple CVs to act upon data communicated between two endpoints without generating an intermediary serializable object. For example, FIG. 4B illustrates an encryption CV 490 and a file CV 492 coupled together between an SO 494 and an encrypted file 496. In one embodiment, encryption CV 490 and file CV 492 are linked to encrypted file 496. In this embodiment, SO 494 may write to or read from encrypted file 496 simply by invoking encryption CV 490. To write to encrypted file 496, SO 494 may output data to encryption CV 490, which encrypts the data. Encryption CV 490 then passes the encrypted data to file CV 492, which converts/formats the encrypted data into encrypted file 496. To read from encrypted file 496, SO 494 may invoke read methods within encryption CV 490, which in turn may invoke read methods within file CV 492, which in turn retrieve the encrypted file data from encrypted file 496. As the data is passed back to SO 494, it is converted/formatted by file CV 492 and decrypted by CV 490. It should be appreciated that in other embodiments, the order of encryption CV 490 and file CV 492 may be swapped.

In one embodiment, converters may be used to perform software upgrades of serializable objects. The converters could be inserted in the execution runtime to perform "in service software upgrades" to translate the serializable objects between version v1 to version v2. Updating an SO may include removing a field with the SO, rearranging the order of one or more fields, adding new fields, or changing the type of a field (i.e., translating the field from one basic type to another). As illustrated in FIG. 4B, upgrades from version v1 to a version v4 may be implemented by linking or daisy chaining converters in series. In this manner, each software release need only create a converter for converting from the previous release.

FIG. 5A illustrates an SO 500, in accordance with an embodiment of the invention. SO 500 represents one possible embodiment of SO 400 or 494 illustrated in FIGS. 4A and 4B. The illustrated embodiment of SO 500 includes a read method, a write method, a to_struct method, a from_struct method, and a plurality of fields 505 (e.g., field 1, field 2, field 3, field 4, etc.). Each field 505 includes a declared variable 510 (e.g., VAR_A, VAR_B, VAR_C, VAR_D, etc.), which may or may not be assigned a field value 515 (e.g., VALUE_A, VALUE_B, VALUE_C, etc.). Assigning a field value 515 to a variable 510 may interchangeably be referred to herein as "setting a field" or "setting a variable."

One or more fields 505 may be marked with an index 520. Indexes 520 are substitute identifiers that may be used to reference the corresponding marked field 505. Indexes 520 enable SO 500 to write out subsets of its fields 505, through a converter, into any other form. In one embodiment, indexes 520 may either represent a primary index or a secondary index. A primary index 520 is an index 520 which may be used to uniquely identify SO 500 from all other SO's. Accordingly, the primary index marks a field 505 having a unique field value 515. In one embodiment, an index value of '1' is reserved for the primary index. The same index value may be used to mark multiple fields 505, as illustrated by index value '2' marking fields 2 and 3. By invoking index value '2', the field values 515 (e.g., VALUE_A and VALUE_B) corresponding to the fields 505 marked with an index 520 having an index value of '2' are referenced.

The to_struct method and the from_struct method may be invoked by SO 500 to convert itself into a fixed length, flat, contiguous memory structure or generate itself from a fixed length, flat, contiguous memory structure, respectively. These methods may be useful for manipulating flat contiguous memory structures in runtime layer 310 (see FIG. 3A), and particularly, for converting an SO in interface layer 320 or management layer 315 into flat structure 350 in runtime layer 310. The to_struct method enables a user to quickly push an SO down into runtime database 330. The to_struct method pre-allocates memory and defines how to map the complex linked memory structures of SO 500 into fixed length, flat, contiguous memory structures, which are amenable to high speed manipulation. The from_struct method may be invoked by a blank or empty SO to populate its fields 505 with data from a flat structure.

In one embodiment, fields 505 may include flags (not illustrated) for identifying each field 505 as "set", "unset", or "modified." When an object reads in an unset field 505 from source object, the reader will simply read in a default value for the unset field, as opposed to reading the unset field 505 from the source object. In contrast, the reader will actually read in field values 515 from a source object for fields 505 marked as "set". The modified flag may be used to indicate whether or not a particular field 505 has been changed, whether or not it is set or unset. For example, a field 505 marked as "unset" and "modified" indicates that a user has explicitly unset a field 505, as opposed to a field 505 that was initialized as "unset" with a default value.

In one embodiment, SO 500 may include a merger function to merger its field values 515 with the field values 515 from another SO. In this case, if a field 505 is flagged as "modified", then it field value 515 is retained, while fields 505 flagged as unmodified will retain existing values. In one embodiment, SO 500 may include a comparison function (e.g., diff_struct), which may be invoked to compare SO 500 against another SO. The output of the comparison function may be a bit field for each field 505, where a '1' represents "is different" and a '0' represents "is same."

FIG. 5B is a table 530 illustrating the basic types of a serializable object, in accordance with an embodiment of the invention. As discussed above, SO 500 may include a number of fields 505 having associated variables 510. Variables 510 may be declared as having one of the basic types listed in table 530. It is noteworthy that basic type number ("BT#") 11, labeled as "complex", is a hierarchical or linked structure basic type that can be defined as a combination of other basic types, including a complex basic type. In this manner, serializable objects may be embedded within other serializable objects as a complex basic type. While table 530 lists 11 basic types, it should be appreciated that table 530 is merely representative and not intended to be a definitive or exhaustive list. Rather, some embodiments may include more, less, or alternative basic types than those listed in table 530.

FIG. 5C illustrates a converter 540, in accordance with an embodiment of the invention. Converter 540 represents one possible embodiment of the converters illustrated in FIGS. 4A and 4B (e.g., DB CV 405, CLI CV 420, NET CV 430, C++ CV 460, file CV 455, C# CV 465, print CV 480, or XML CV 470). The illustrated embodiment of converter 540 includes a plurality of read methods 550 for reading each of the basic types listed in table 530 (e.g., read BT(1), read BT(2) . . . , read BT(N)) and a plurality of write methods 555 for writing each of the basic types listed in table 530 (e.g., write BT(1), write BT(2) . . . , write BT(N)). Converter 540 accepts field values 515 and their corresponding variable names 510 as inputs and converter these inputs to a specific form. Accordingly, SO 500 can call converter 540 on each of its fields 505 or a subset of its fields 505 to convert itself, in whole or in part, to some other form.

Operation of converter 540 to write from or read into SO 500 is now described with reference to FIGS. 6A, 6B, and 6C. FIG. 6A is a flow chart illustrating a process 605 for writing from SO 500, in accordance with an embodiment of the invention. In a process block 610, one or more fields within SO 500 are "set" or assigned specific field values 515. In a process block 520, the write method within SO 500 is invoked, which in turn will invoke converter 540 (process block 620).

Once invoked, converter 540 will execute a corresponding one of its write methods on each set field 505 in SO 500. For example, if VAR_A was declared as basic type INT64 (i.e., 64 bit integer), then converter 540 will invoke WRITE BT(4), corresponding to INT64 in table 530. Similarly, if VAR_B was declared as basic type BOOLEAN, then converter 540 will invoke WRITE BT(10), corresponding to basic type BOOLEAN in table 530. Each write method 555 invoked by converter 540 will access the corresponding field 505, convert the contents of the field based on the converter type, and write out the converted field to the destination object/file (process block 625).

In one embodiment, specific fields 505 of SO 500 may be referenced to be written out by specifying corresponding indexes 520. For example, by invoking a write method, identifying a particular converter, and passing one or more index values to the write method, specified fields 505 may be written out from SO 500, while skipping others. In one embodiment, the default setting is writing out all fields 505 when a write method is invoked, without specifying index values. In one embodiment, all fields 505 may be written out by passing a default index number, such as '0'.

FIG. 6B illustrates how each fields 505 of SO 500 are independently passed into the corresponding write methods 555 of converter 540. In one embodiment, if CV 540 is a database converter (e.g., DB CV 405), then fields 505 are serialized and flattened into a flat database structure 630. In one embodiment, if CV 540 is a C++ converter (e.g., C++ CV 460), then fields 505 are converted into fields of a C++ object/file 635. In one embodiment, if CV 540 is an XML converter (e.g., XML CV 470), then fields 505 are converted into attributes of an XML object/file 640.

FIG. 6C is a flow chart illustrating a process 650 for reading field values into SO 500, in accordance with an embodiment of the invention. To commence reading field values 515 into SO 500, the read method of SO 500 is invoked (process block 655) and a converter identified (process block 660). As discussed above, converters (e.g., CV 540) may be pre-generated and linked to a source file or object. Therefore, once the read method is invoked and a specific converter identified, data from the source object/file is read into SO 500 through the specified converter (process 655). In one embodiment, the read method of SO 500 invokes corresponding read methods 550 within converter 540 to read in each field value 515. As each read method 550 of converter 540 is invoked, it converts the basic types from the format of the source object/file to the format of SO 500. In one embodiment, only specified fields 505 may be populated with read in values by passing index values 520 to the read method of SO 500.

As discussed above, to translate SO 500 from interface layer 320 or management layer 315 to runtime layer 310, SO 500 may be converted into a flat structure using the to_struct method ( ). There may some scenarios where it may be desirable to store more than one type of SO into runtime database 330. This may be achieved using a concept referred as "union". From interface layer 320 or management layer 315 records may be passed down to runtime layer 310 that contain multiple types. For example,

```
Class Foo
{
    Key      *key;
    Record   *data;
};
```

The types Key and Record are base classes of a serializable object language ("SOL"). The class Foo can contain many different types of Key and many different types of Record, such as,

```
MyRecord: public Record
{
   //My special data;
};
MyKey: public Key
{
   //My special data;
};
```

So, there could be MyKey, YourKey, HisKey, MyRecord, YourRecord, HisRecord, or the like. Therefore, the class Foo could be made up of any mixture of these types, since they inherit from Key and Record. This is referred to as "polymorphism." In order to translate Foo into runtime database 330, Foo is converted into a flat structure, which then gets stored into runtime database 330. This may be achieved by marking the class Foo with a special attribute, such as,

```
class Foo
{
    [SOField(union=MyKey, YourKey, HisKey)]
```

-continued

```
        Key         *key;
        [SOField(union=MyRecord, YourRecord, HisRecord)]
        Record      *data;
    };
```

With this special attribute an SOL compiler can automatically generate code that will result in,

```
class Foo
{
    struct _type
    {
    enum which_t { MYKEY, YOURKEY, HISKEY };
    which_key_t isset;
    union _u1
    {
    MyKey::_type       mykey;
    YourKey::_type     yourkey;
    HisKey::_type      hiskey;
    }
    enum which_t { MYRECORD, YOURRECORD, HISRECORD };
    which_record_t isset1;
    union _u2
    {
    MyRecord::_type    myrecord;
    YourRecord::_type  yourrecord;
    HisRecord::_type   hisrecord;
    }
    };
    Key         *key;
    Record      *data;
};
```

The _type structure represents the flat union for storage into runtime database 330. The SOL compiler may generate serialization code that will move back and forth from the _type::_u1 and _type::_u2 into the correct kind of objects in the Key *key and Record *data fields. For example, if *key contained a MyKey, then the generated code may perform a to_struct( ) call from the *key (which is a MyKey) into the field _type::_u1::mykey. Next, the generated code would set the which_key_t field to be equal to MYKEY. On the way back, the generate code would look at the which_key_t field and switch on the type,

```
    Switch (which)
    {
        Key     *whichkey;
        case    MYKEY:
                Whichkey = new MyKey;
                Whichkey –> fromstruct (_type::_u1::mykey);
        case YOURKEY:
        case HISKEY:
    }
    key = whichkey;.
```

In one embodiment, the above functionality may be embedded within SO 500 and invoked by calling a to_union ( ) method or a from_union ( ) method. The to_union ( ) and from_union ( ) methods enable moving from a choice of structures into a union automatically and facilitates transferring objects from interface layer 320 through management layer 315 and down to runtime layer 310 into runtime database 330.

Figure 7:
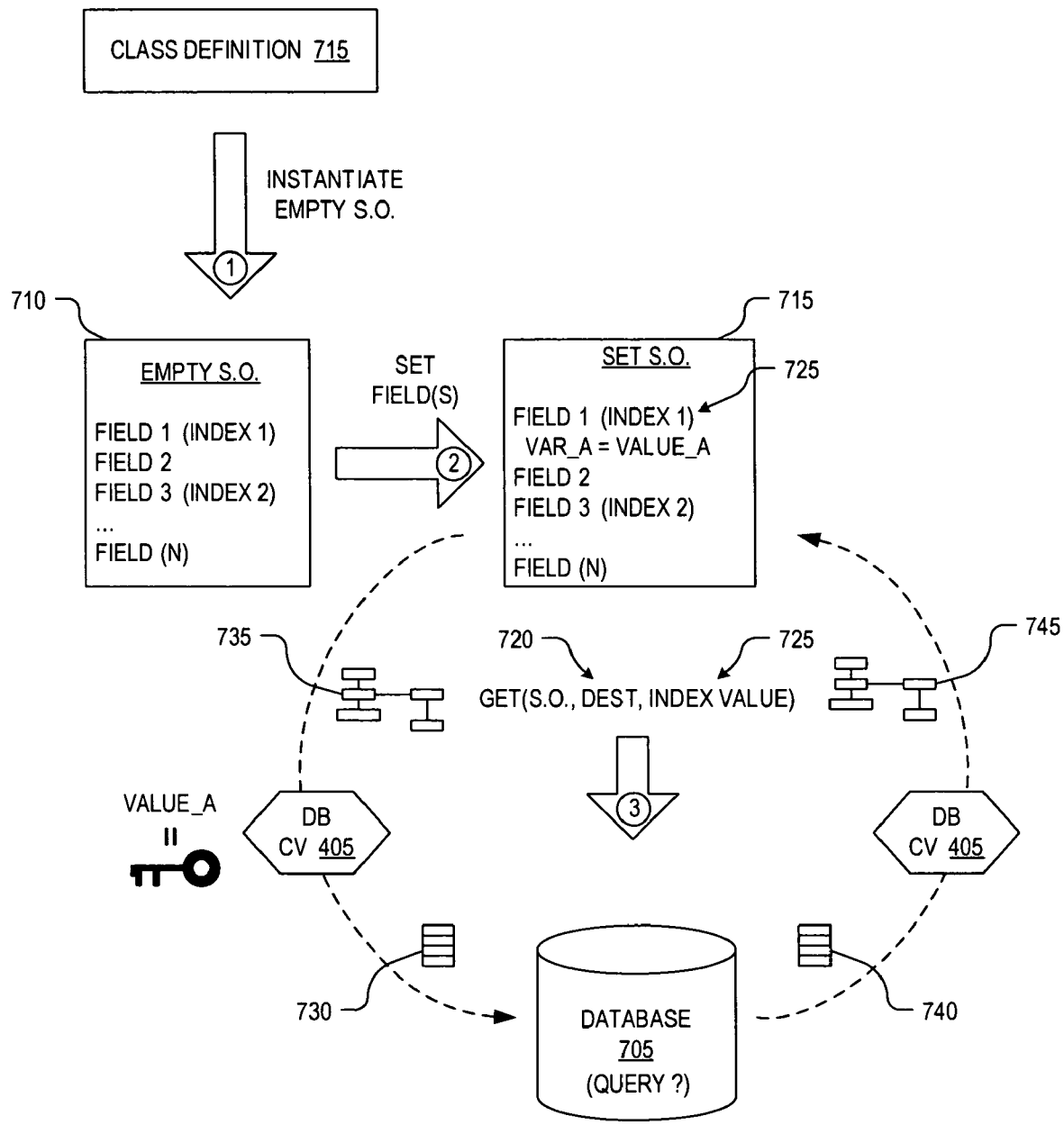
FIG. 7 is a block diagram illustrating a technique for reading a serializable object from a database, in accordance with an embodiment of the invention.
Figure 8:
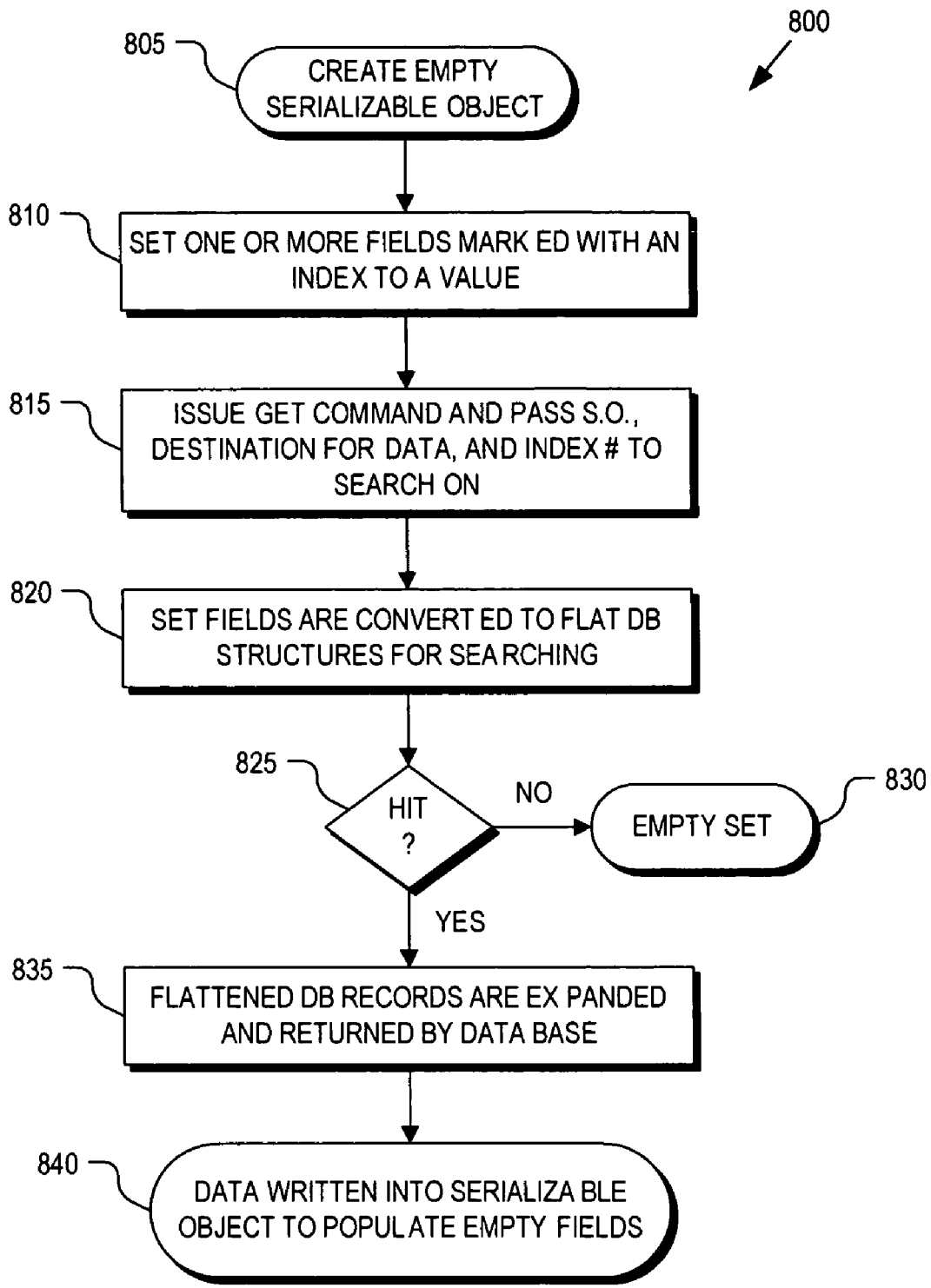
FIG. 8 is a flow chart illustrating a process for reading a serializable object from a database, in accordance with an embodiment of the invention.

FIGS. 7 and 8 illustrate a technique for reading a serializable object from a database 705, in accordance with an embodiment of the invention. FIG. 7 is a block diagram illustrating the technique, while FIG. 8 illustrates a process 800 for the same. The order in which some or all of the process blocks appear in each process described herein should not be deemed limiting. Rather, one of ordinary skill in the art having the benefit of the present disclosure will understand that some of the process blocks may be executed in a variety of orders not illustrated.

In a process block 805, an empty SO 710 is created (illustrated in FIG. 7 by arrow 1). An empty SO is a serializable object where none of the fields have been set or assigned field values. Empty SO 710 may be created by instantiating a new SO based on a class definition file 715. In a process block 810, one or more fields of empty SO 710 (e.g., fields 505) are set or assigned field values (illustrated in FIG. 7 by arrow 2) to create set SO 715. In the embodiment illustrated in FIG. 7, field 1 is set with a field value "VALUE_A." In a process block 815, a GET command is issued on database 705 (illustrated in FIG. 7 by arrow 3) to retrieve data from database 705. In one embodiment, the GET command may be invoked from interface layer 320 via the MLAPI.

In one embodiment, the GET command is passed set SO 715, a destination address or pointer 720 to a destination object to which database 705 should return the data, and one or more index values 725. The destination object may be set SO 715 itself, or some other object or file. Index value(s) 725 passed into the GET command indicates to database 705 which fields 505 of all the objects stored in database 705 it should inspect and attempt to match against the set fields of set SO 715. The set field value (e.g., VALUE_A) operates as the key for searching database 705 to find any SO stored therein having a field marked with an index value matching index value 725 (e.g., index 1) and having a corresponding field value matching field value VALUE_A. Accordingly, a user of database 705 can query database 705 using the data, itself, rather than using an extraneous or separate key. Furthermore, even though multiple fields of set SO 715 may be set with field values, by selecting different index values corresponding to different fields, a particular record (e.g., serializable object) stored in database 705 can be searched for using a variety of different data as the key. Fields 505 marked with the primary or secondary indexes provide search flexibility to the end user to query database 705 based on a variety of different subsets of the data/fields within set SO 715.

For example, database 705 may store phone records that include the following three fields: a name field, a phone number field, and an address field. If the name fields are marked with index value 1, the phone number fields are marked with index value 2, and the address fields are marked with index value 3, then a user who wishes to determine the phone number associated with a particular name would set the first field with the name and pass the set SO to the GET command. Since the name field is marked with an index value 1, index value 725 would be passed as a '1' into the GET command. Of course, the user could also set the address field and/or phone number field, pass the set SO to the GET command, and retrieve the corresponding name.

Returning to FIG. 8, in a process block 820, the one or more set fields marked with index value(s) 725 is/are converted to flat contiguous memory structure(s) 730 by database CV 405. As illustrated, serializable objects that exist outside of database 705 may exist as link memory structures 735, which are serialized into flat contiguous memory structures 730 prior to passing into database 705. Although DB CV 405 is illustrated as external to database 705, it should be appreciated that DB CV 405 may in fact be an internal component to database 705. Once passed into database 705 by the GET command, a query is executed to determine whether a matching record index value/field value pair exists (decision block 825). If such a record is not found, then an empty set, null, or void response is returned to the destination object in a process block 830. If such a record is found, then process 800 continues to a process block 835.

In process block 835, the matching record (or records) is converted from a flat contiguous memory structure 740 into a more complex linked memory structure 745 by DB CV 405 and returned to the destination object (illustrated as set SO 715 in FIG. 7). Finally, in a process block 840, the data from the matching record is written into the destination object to populate the empty fields of set SO 715 with field values from the matching record stored in database 705.

Figure 9:
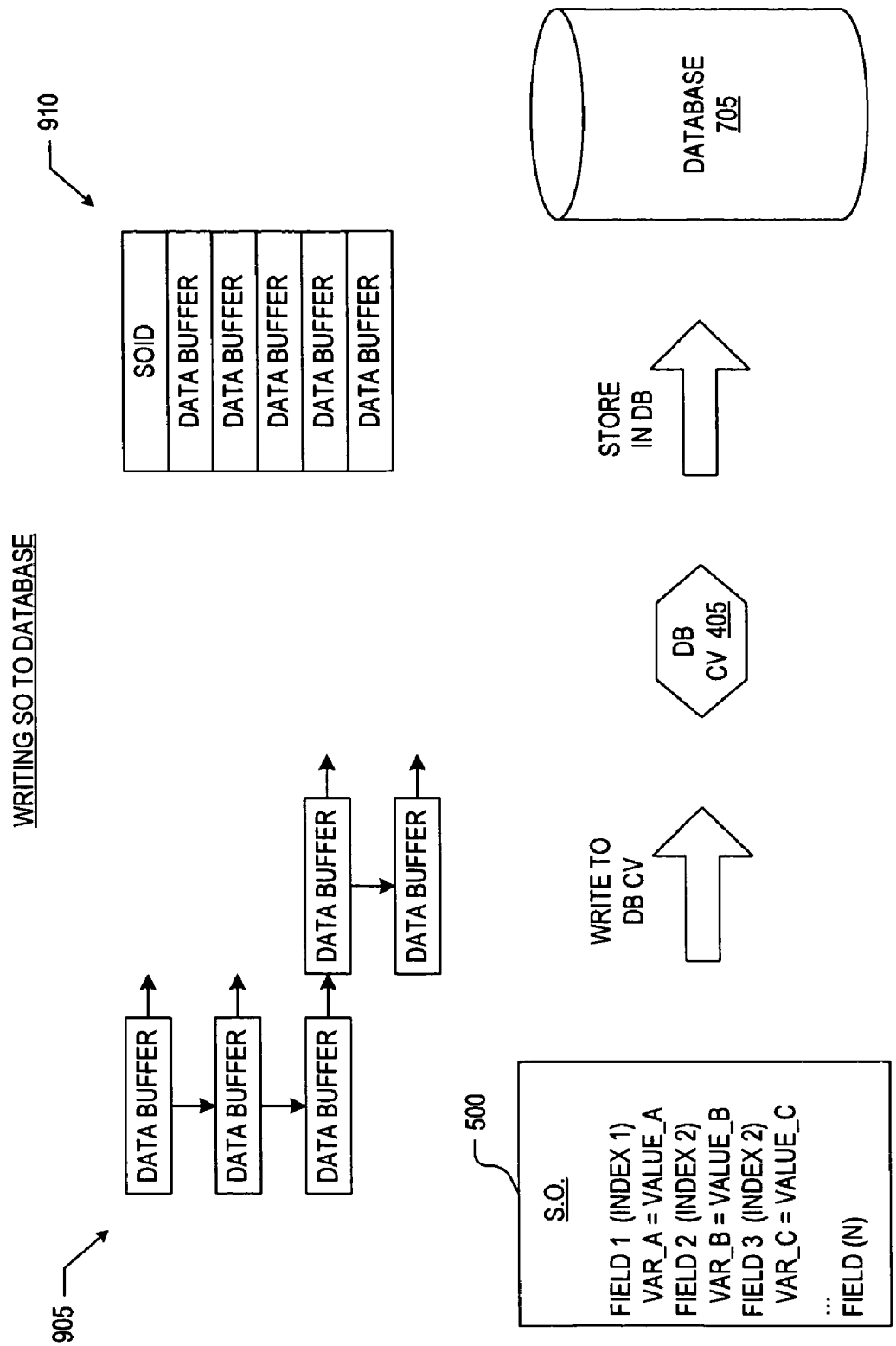
FIG. 9 is a block diagram illustrating a technique for writing a serializable object into a database, in accordance with an embodiment of the invention.
Figure 10:
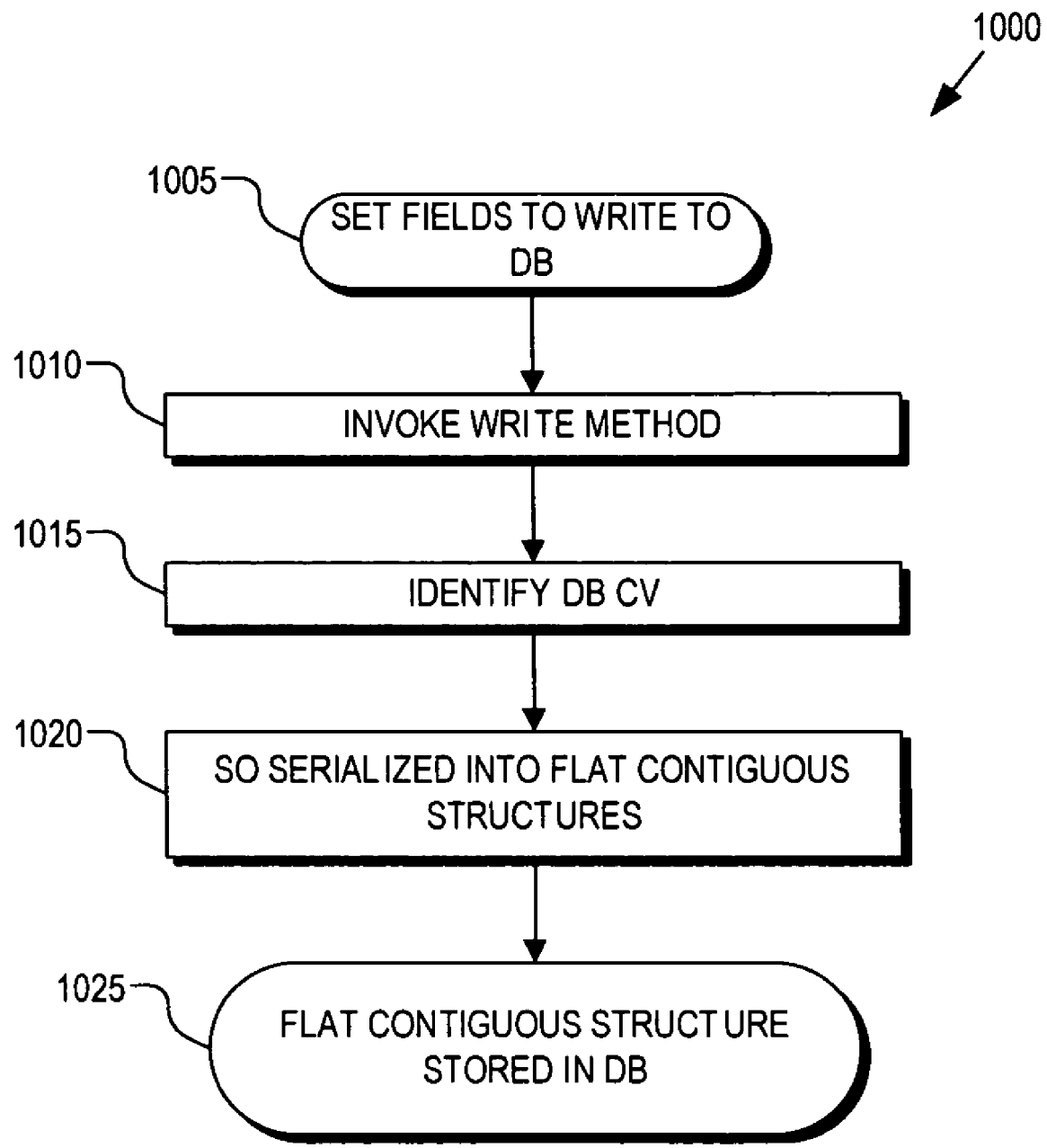
FIG. 10 is a flow chart illustrating a process for writing a serializable object into a database, in accordance with an embodiment of the invention.

FIGS. 9 and 10 illustrate a technique for writing SO 500 into database 705, in accordance with an embodiment of the invention. FIG. 9 is a block diagram illustrating the technique, while FIG. 10 illustrates a process 1000 for the same. In a process block 1005, one or more fields 505 within SO 500 are set. Once fields 505 are set, the write method within SO 500 may be invoked (process block 1010) and database CV 405 identified (process block 1015). Once invoked, database CV 405 converts the complex linked memory structures 905 of SO 500 into a flat contiguous memory structure 910 (process block 1020) and stores flat contiguous memory structure 910 in database 705 (process block 1025). In one embodiment, database CV 405 may be internal to database 705, rather than external as illustrated. In one embodiment, an SO identifier ("SOID") is tagged onto flat contiguous memory structure 910 prior to storing flat contiguous memory structure 910 into database 705 as a record. The SOID is a unique ID, which may also be referenced when retrieving a stored record.

In one embodiment, SO 500 may be written into database 705 by invoking the CREATE command published by the MLAPI into interface layer 320. In this embodiment, the CREATE command may be passed SO 500 and one or more index values to identify which fields 505 are to be written into database 705. In this manner, a subset of the data or fields 505 within SO 500 may be written into database 705.

Figure 11:
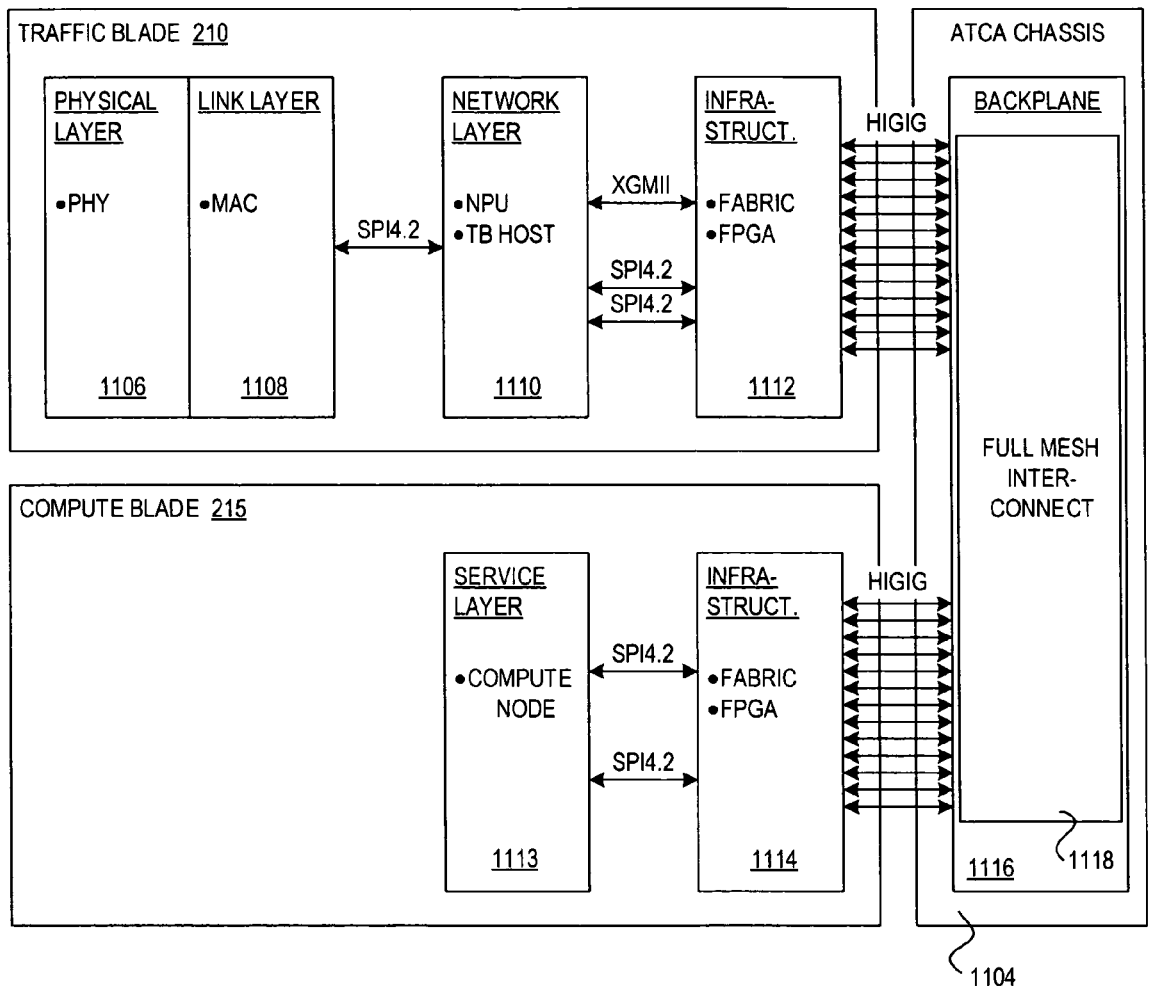
FIG. 11 is a block diagram illustrating interconnections between traffic modules and compute modules of a network service node, in accordance with an embodiment of the invention.

In accordance with architecture aspects of some embodiments, the aforementioned functions may be facilitated by various processing and storage resources hosted by associated line cards and the like, which are mounted in a common chassis. As shown in FIG. 11, from a datapath perspective, the hardware architecture of one embodiment of network service node 200 can be decomposed into three entities, Traffic Blades (TB) 210, Compute Blades (CB) 215 and the chassis 1104. A TB 210 can be further reduced to its physical and link layer portions 1106 and 1108, network layer components 1110, and infrastructure components 1112. Similarly, a CB 215 provides Service Layer termination 1113 and infrastructure components 1114. In one embodiment, a CB can be further re-defined to be an OAMP Blade based on its slot index (within chassis 1104). OAMP blades are a functional superset of CBs, adding operations, administration, maintenance, and provisioning functionality (collectively referred to as OAMP card function or OAMP CF).

As illustrated in the embodiments herein, chassis 1104 comprises an Advanced Telecommunication and Computing Architecture (ATCA or AdvancedTCA®) chassis. The ATCA Chassis provides physical connectivity between the blades via a passive backplane 1116 including a full-mesh interconnect 1118. It is noted that the ATCA environment depicted herein is merely illustrative of one modular board environment in which the principles and teachings of the embodiments of the invention described herein may be applied. In general, similar configurations may be deployed for other standardized and proprietary board environments, including but not limited to blade server environments.

The ATCA 3.0 base specification (approved Dec. 30, 2002), which is being carried out by the PCI Industrial Computer Manufacturers Group ("PICMG"), defines the physical and electrical characteristics of an off-the-shelf, modular chassis based on switch fabric connections between hot-swappable blades. (As used herein, the terms "board," "blade," and "card," are interchangeable.) This specification defines the frame (rack) and shelf (chassis) form factors, core backplane fabric connectivity, power, cooling, management interfaces, and the electromechanical specification of the ATCA-compliant boards. The electromechanical specification is based on the existing IEC60297 EuroCard form factor, and enables equipment from different vendors to be incorporated in a modular fashion with guaranteed interoperability. The ATCA 3.0 base specification also defines a power budget of 200 Watts (W) per board, enabling high performance servers with multi-processor architectures and multi gigabytes of on-board memory.

In addition to power input to ATCA boards, mating connectors on the boards and backplane are employed for coupling input/output (I/O) signals. Many of the ATCA boards, as well as other modular boards used for telecommunications and computer, such as but not limited to CompactPCI, employ very-high speed I/O channels. For example, Advanced Switching ("AS") employs a serial communication channel operating at Gigahertz+ frequencies. ATCA boards may also provide one or more I/O ports on their front panels, enabling an ATCA board to be coupled to other network resources.

Figure 12:
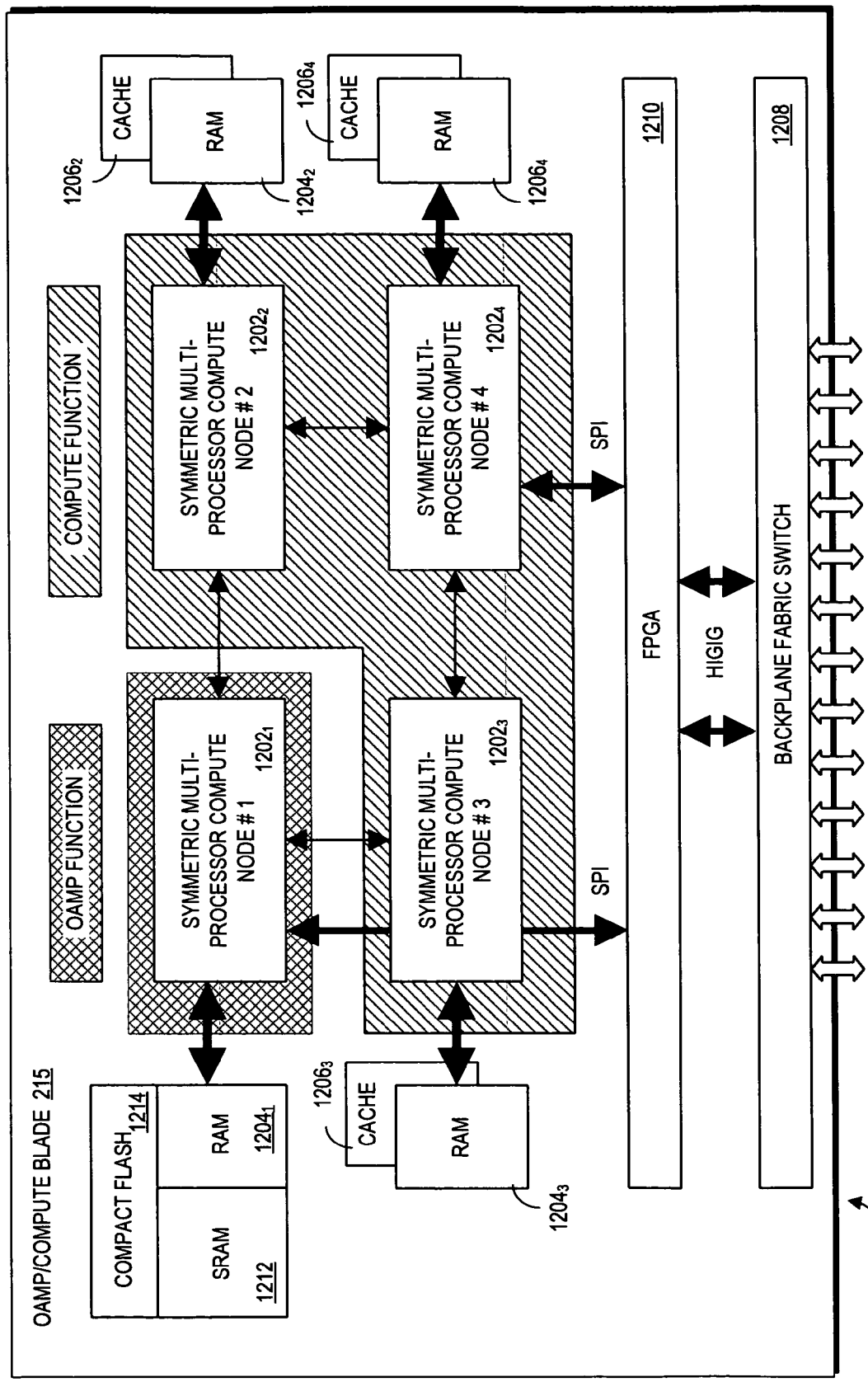
FIG. 12 is a block diagram illustrating a compute module, in accordance with an embodiment of the invention.

An exemplary architecture 1200 for a compute blade 215 is shown in FIG. 12. In one embodiment, a single compute blade (physical) architecture is employed for both Compute Blades and OAMP CF's. More particularly, under architecture 1200, a corresponding blade may be deployed to support both Compute Blade and OAMP functionality.

Compute Blade 215 employs four multiple processor compute nodes $1202_{1-4}$. In general, each of compute nodes $1202_{1-4}$ functions as multiple processor resources, with each processor resource being associated with a logical processor. Accordingly, such processor resources may be implemented using separate processors, or processor chips employing multiple processor cores. For example, in the illustrated embodiment of FIG. 13, each of compute nodes $1202_{1-4}$ is implemented via an associated symmetric multi-core processor. Exemplary multi-core processors that may be implemented include, but are not limited to Broadcom 1480 and 1280 devices. Each of the compute nodes $1202_{1-4}$ is enabled to communicate with other compute nodes via an appropriate interface (e.g., bus or serial-based interfaces). For the Broadcom 1480 and 1280 devices, this interface comprises a "Hyper Transport" (HT) interface. Other native (standard or proprietary) interfaces between processors may also be employed.

As further depicted in architecture 1200, each compute nodes $1202_{1-4}$ is allocated various memory resources, including respective RAM $1204_{1-4}$. Under various implementations, each of compute nodes $1202_{1-4}$ may also be allocated an external cache $1206_{1-4}$, or may provide one or more levels of cache on-chip. In one embodiment, the RAM comprises ECC (Error Correction Code) RAM. In one embodiment, each compute node employs a NUMA (Non-Uniform Memory Access) cache coherency scheme. Other cache coherency schemes, such as MESI (Modified, Exclusive, Shared, Invalidated), may also be implemented for other embodiments.

Each Compute Blade 215 includes a means for interfacing with ATCA mesh interconnect 1118. In the illustrated embodiment of FIG. 12, this is facilitated by a Backplane Fabric Switch 1208. Meanwhile, a field programmable gate array ("FPGA") 1210 containing appropriate programmed logic is used as an intermediary component to enable each of compute nodes $1202_{1-4}$ to access backplane fabric switch 1208 using native interfaces for each of the compute nodes and the fabric switch. In the illustrated embodiment, the interface between each of compute nodes $1202_{1-4}$ and the FPGA 1210 comprises an SPI (System Packet Interface) 4.2 interface, while the interface between the FPGA and backplane fabric switch 1208 comprises a Broadcom HiGig™ interface. It is noted that these interfaces are merely exemplary, and that other interface may be employed depending on the native interfaces of the various blade components.

In addition to local RAM (e.g., RAM $1204_1$), the compute node associated with the OAMP function (depicted in FIG. 12 as Compute Node #1) is provided with local SRAM 1212 and a non-volatile store (depicted as Compact flash 1214). The non-volatile store is used to store persistent data used for the OAMP function, such as provisioning information and logs. In Compute Blades that do not support the OAMP function, each compute node is provided with local RAM and a local cache.

In the embodiment illustrated in FIG. 12, compute blade 215 is provisioned as an OAMP blade. In one configuration (as shown), one of the compute nodes is employed for performing OAMP functions (e.g., compute node $1202_1$), while the other three compute nodes (e.g., compute nodes $1202_{2-4}$) perform normal compute functions associated with compute blades, as described in further detail below. When a compute blade 215 is provisioned as a compute blade, each of compute nodes $1202_{1-4}$ is available for performing the compute functions described herein.

Figure 13:
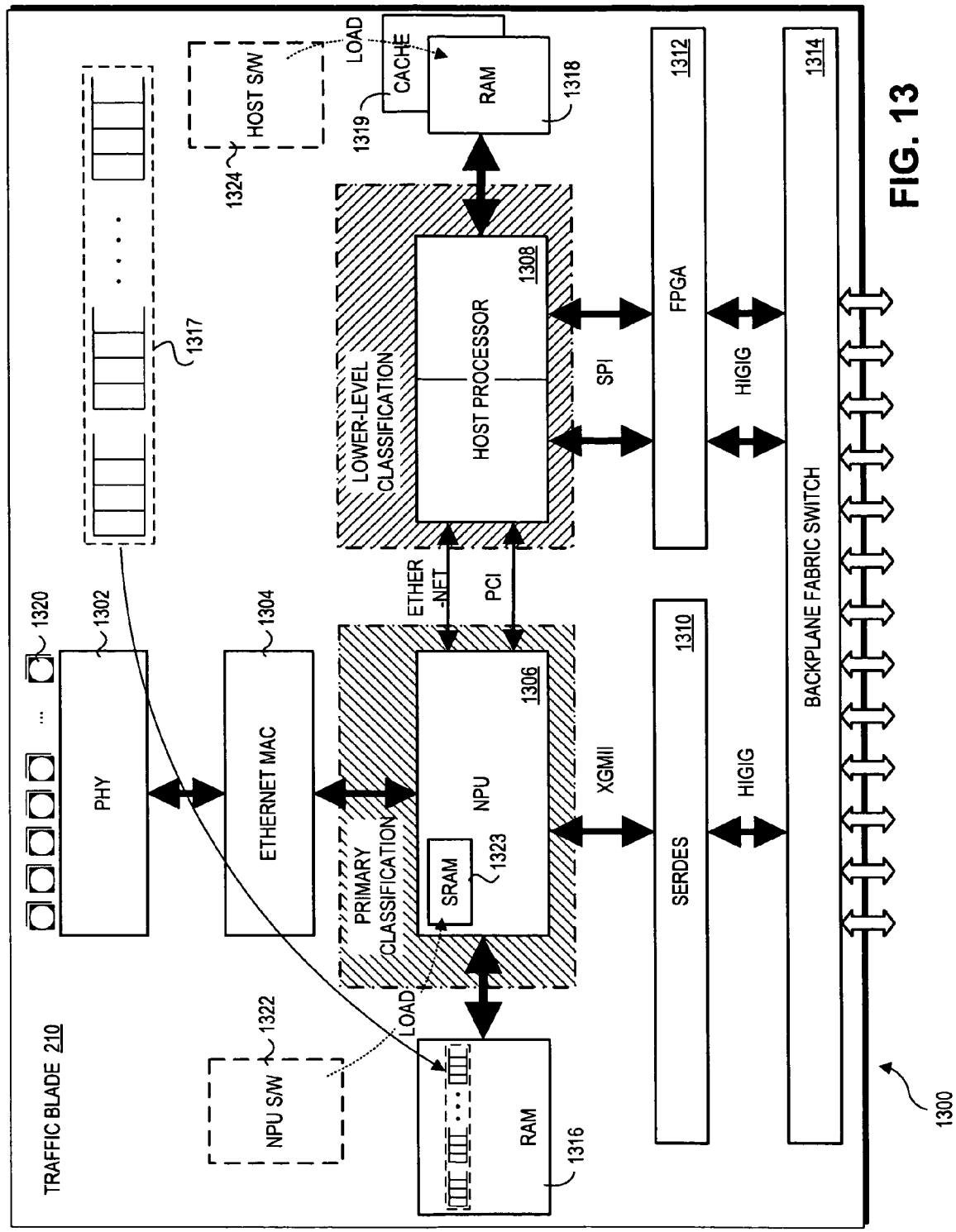
FIG. 13 is a block diagram illustrating a traffic module, in accordance with an embodiment of the invention.

FIG. 13 shows an exemplary architecture 1300 for a traffic blade 210. Architecture 1300 includes a PHY block 1302, an Ethernet MAC block 1304, a network processor unit (NPU) 1306, a host processor 1308, a SERDES interface 1310, an FPGA 1312, a backplane fabric switch 1314, RAM 1316 and 1318 and cache 1319. The traffic blade further includes one or more I/O ports 1320, which are operatively coupled to PHY block 1320. Depending on the particular use, the number of I/O ports may vary from 1 to N ports. For example, under one traffic blade type a 10×1 Gigabit Ethernet (GigE) port configuration is provided, while for another type a 1×10 GigE port configuration is provided. Other port number and speed combinations may also be employed.

PHY block 1302 and Ethernet MAC block 1304 respectively perform layer 1 (Physical) and layer 2 (Data Link) functions, which are well-known in the art. In general, the PHY and Ethernet MAC functions may be implemented in hardware via separate components or a single component, or may be implemented in a combination of hardware and software via an embedded processor or the like.

One of the operations performed by a traffic blade is packet identification/classification. As discussed above, a multi-level classification hierarchy scheme is implemented for this purpose. Typically, a first level of classification, such as a 5-Tuple signature classification scheme, is performed by the traffic blade's NPU 1306. Additional classification operations in the classification hierarchy may be required to fully classify a packet (e.g., identify an application flow type). In general, these higher-level classification operations may be performed by the traffic blade's host processor 1308 and/or a processor on a compute blade, depending on the particular classification.

NPU 1306 includes various interfaces for communicating with other board components. These include an Ethernet MAC interface, a memory controller (not shown) to access RAM 1316, Ethernet and PCI interfaces to communicate with host processor 1308, and an XGMII interface. SERDES interface 1310 provides the interface between XGMII signals and HiGig signals, thus enabling NPU 1306 to communicate with backplane fabric switch 1314. NPU 1306 may also provide additional interfaces to interface with other components, such as an SRAM (Static Random Access Memory) interface unit to interface with off-chip SRAM (both not shown).

Similarly, host processor 1308 includes various interfaces for communicating with other board components. These include the aforementioned Ethernet and PCI interfaces to communicate with NPU 1306, a memory controller (on-chip or off-chip—not shown) to access RAM 1318, and a pair of SPI 4.2 interfaces. FPGA 1312 is employed to as an interface between the SPI 4.2 interface signals and the HiGig interface signals.

Typically, NPUs are designed for performing particular tasks in a very efficient manner. These tasks include packet forwarding and packet classification, among other tasks related to packet processing. To support such functionality, NPU 1306 executes corresponding NPU software 1322. This software is shown in dashed outline to indicate that the software may be stored (persist) on a given traffic blade (e.g., in a flash device or the like), or may be downloaded from an external (to the traffic blade) store during initialization operations, as described below. During run-time execution, NPU software 1322 is loaded into internal SRAM 1323 provided by NPU 1306.

Host processor 1308 is employed for various purposes, including lower-level (in the hierarchy) packet classification, gathering and correlation of flow statistics, and application of traffic profiles. Host processor 1308 may also be employed for other purposes. In general, host processor 1308 will comprise a general-purpose processor or the like, and may include one or more compute cores (as illustrated, in one embodiment a two-core processor is used). As with NPU 1306, the functionality performed by host processor is effected via execution of corresponding software (e.g., machine code and or virtual machine byte code), which is depicted as host software 1324. As before, this software may already reside on a traffic blade, or be loaded during blade initialization.

In one embodiment, host processor 1308 is responsible for initializing and configuring NPU 1306. Under one initialization scheme, host processor 1308 performs network booting via the DHCP (or BOOTP) protocol. During the network boot process, an operating system is loaded into RAM 1318 and is booted. The host processor then configures and initializes NPU 1306 via the PCI interface. Once initialized, NPU 1306 may execute NPU software 1322 on a run-time basis, without the need or use of an operating system.

The processes explained above are described in terms of computer software and hardware. The techniques described may constitute machine-executable instructions embodied within a machine (e.g., computer) readable medium, that when executed by a machine will cause the machine to perform the operations described. Additionally, the processes may be embodied within hardware, such as an application specific integrated circuit ("ASIC") or the like.

A machine-accessible medium includes any mechanism that provides (i.e., stores) information in a form accessible by a machine (e.g., a computer, network device, personal digital assistant, manufacturing tool, any device with a set of one or more processors, etc.). For example, a machine-accessible medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

We claim:

1. A computer implemented method to access a database of records, comprising:

executing by the database a command including a field value and an index value, wherein multiple fields of an object are marked with a same index value, the database storing flat contiguous memory structures as records, each of the flat contiguous memory structures converted from field values of a respective object by a database converter;

passing multiple field values to the database, the multiple field values corresponding to the multiple fields of the object marked with the same index value;

searching the database to determine whether any of the records stored in the database include the multiple field values in matching fields indicated by the index value;

where the searching determines that the database includes at least one record with the field values in matching fields indicated by the same index value, returning the at least one record stored in the database as one of the flat contiguous memory structures;

in response to the returning the at least one record, calling a method of the object to convert the at least one record from the one of the flat contiguous memory structures into a complex of linked memory structures; and providing the complex of linked memory structures for populating a plurality of fields of the object.

2. The computer implemented method of claim 1, further comprising:

creating the object as an empty object with unset empty fields; and setting a selected field from among the unset empty fields with the field value, wherein the field value functions as a key for searching the database.

3. The computer implemented method of claim 2, wherein the records stored in the database are stored as flat contiguous memory structures, the method further comprising:

converting the field value to a flat contiguous memory structure prior to searching the database with the field value.

4. The computer implemented method of claim 2, further comprising passing to the command the index number, the object with the selected field set, and a destination object to which the plurality of field values should be returned, wherein the index number defaults to a primary index associated with a unique field value in the database, if the index number is not provided.

5. The computer implemented method of claim 1, wherein the object comprises a serializable object.

6. The computer implemented method of claim 1, further comprising:

setting a selected field from among a plurality of fields in the object; and writing only the field value of the selected field to the database.

7. The computer implemented method of claim 1, wherein the database comprises a provisioning database and wherein the records comprise provisioning records for provisioning a network service node to couple between at least two networks.

8. The computer implemented method of claim 1, wherein the database comprises a runtime database and wherein the records comprise runtime data of a network service node to couple between at least two networks.

9. The computer implemented method of claim 1, wherein the database is accessible through a management layer application programming interface ("MLAPI"), the method further comprising:

providing an extensible markup language ("XML") file at an interface layer;

invoking a create command published by the MLAPI to the interface layer;

converting the XML file to the object;

converting the object to a flat contiguous memory structure; and storing the flat contiguous memory structure to the database.

10. A machine-accessible storage medium that provides instructions that, if executed by a machine, will cause the machine to perform operations comprising:

executing by the database a command including a field value and an index value, wherein multiple fields of an object are marked with a same index value, the database storing flat contiguous memory structures as records, each of the flat contiguous memory structures converted from field values of a respective object by a database converter;

passing multiple field values to the database, the multiple field values corresponding to the multiple fields of the object marked with the same index value;

searching the database to determine whether any of the records stored in the database include the multiple field values in matching fields indicated by the index value;

where the searching determines that the database includes at least one record with the field values in matching fields indicated by the same index value, returning the at least one record stored in the database as one of the flat contiguous memory structures;

in response to the returning the at least one record, calling a method of the object to convert the at least one record from the one of the flat contiguous memory structures into a complex of linked memory structures; and providing the complex of linked memory structures for populating a plurality of fields of the object.

11. The machine-accessible storage medium of claim 10, further providing instructions that, if executed by the machine, will cause the machine to perform further operations, comprising:

creating the object as an empty object with unset empty fields; and setting a selected field from among the unset empty fields with the field value, wherein the field value functions as a key for searching the database.

12. The machine-accessible storage medium of claim 11, wherein the records stored in the database are stored as flat contiguous memory structures, and further providing instructions that, if executed by the machine, will cause the machine to perform further operations, comprising:

converting the field value to a flat contiguous memory structure prior to searching the database with the field value.

13. The machine-accessible storage medium of claim 11, further providing instructions that, if executed by the machine, will cause the machine to perform further operations, comprising:

passing to the command the index number, the object with the selected field set, and a destination object to which the plurality of field values should be returned, wherein the index number defaults to a primary index associated with a unique field value in the database, if the index number is not provided.

14. The machine-accessible storage medium of claim 10, wherein the object comprises a serializable object.

15. The machine-accessible storage medium of claim 10, further providing instructions that, if executed by the machine, will cause the machine to perform further operations, comprising:

setting a selected field from among a plurality of fields in the object; and writing only the field value of the selected field to the database.

16. The machine-accessible storage medium of claim 10, wherein the database is accessible through a management layer application programming interface ("MLAPI"), and further providing instructions that, if executed by the machine, will cause the machine to perform further operations, comprising:

providing an extensible markup language ("XML") file at an interface layer;

invoking a create command published by the MLAPI to the interface layer;

converting the XML file to the object;

converting the object to a flat contiguous memory structure; and storing the flat contiguous memory structure to the database.

* * * * *